United States Patent [19]

Sprecker

[11] 4,375,004
[45] * Feb. 22, 1983

[54] NORBORNYL ALKYL ETHERS

[75] Inventor: Mark A. Sprecker, Sea Bright, N.J.

[73] Assignee: International Flavors & Fragrances Inc., New York, N.Y.

[*] Notice: The portion of the term of this patent subsequent to Jan. 19, 1999, has been disclaimed.

[21] Appl. No.: 313,722

[22] Filed: Oct. 22, 1981

Related U.S. Application Data

[63] Continuation-in-part of Ser. No. 200,012, Oct. 23, 1980, Pat. No. 4,311,861.

[51] Int. Cl.³ ............................................. C07C 43/18
[52] U.S. Cl. .................................................. 568/665
[58] Field of Search ..................... 568/665; 252/522 R

[56] References Cited

U.S. PATENT DOCUMENTS 4,311,861  1/1982  Sprecker .............................. 568/666

FOREIGN PATENT DOCUMENTS 49-20571  5/1974  Japan .

OTHER PUBLICATIONS

Shield, Can. Jour. Chem., vol. 49, (1971), 1142.

*Primary Examiner*—Bernard Helfin
*Attorney, Agent, or Firm*—Arthur L. Liberman

[57] ABSTRACT

Described are the compounds having the structures:

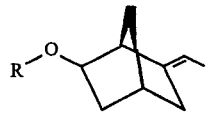

and

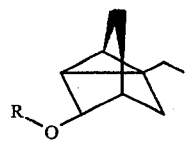

wherein R represents isopropyl as well as a process for preparing such compounds.

3 Claims, 8 Drawing Figures

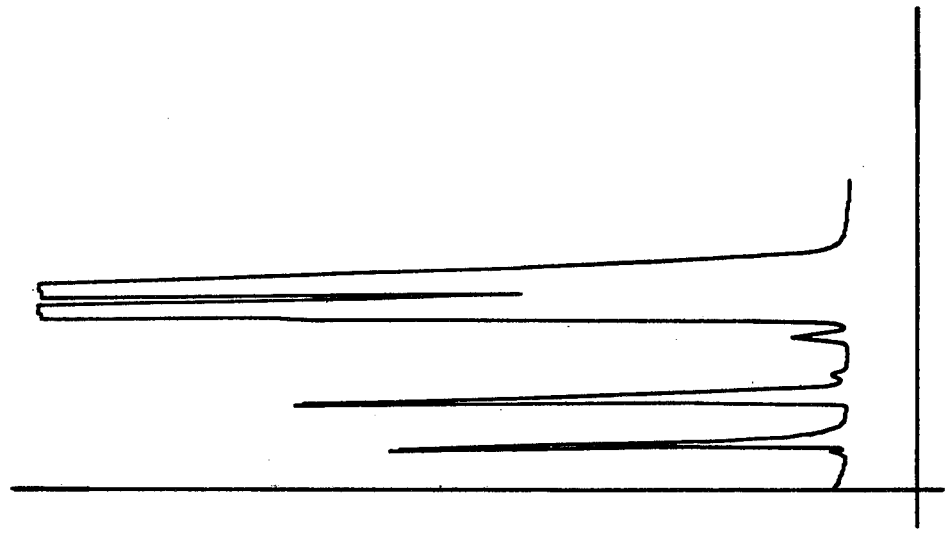
FIG. IA
GLC PROFILE FOR EXAMPLE I.
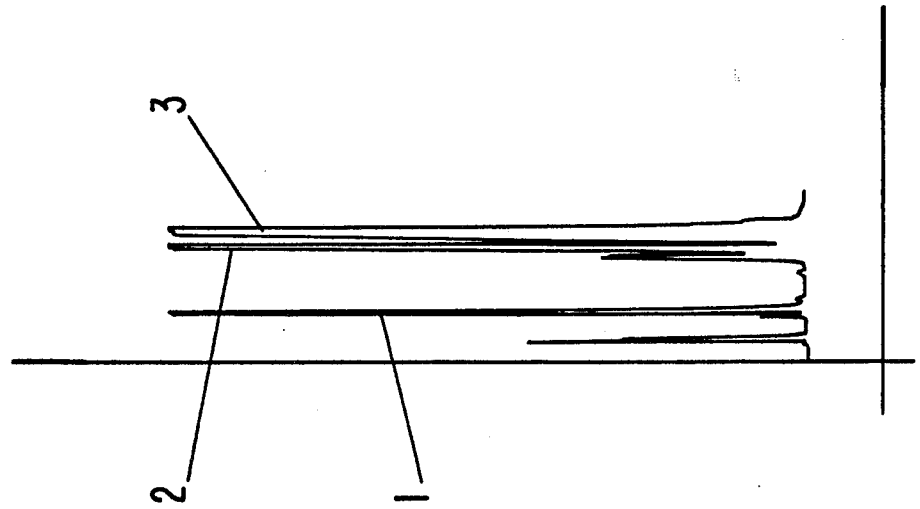
FIG. I
GLC PROFILE FOR EXAMPLE I.

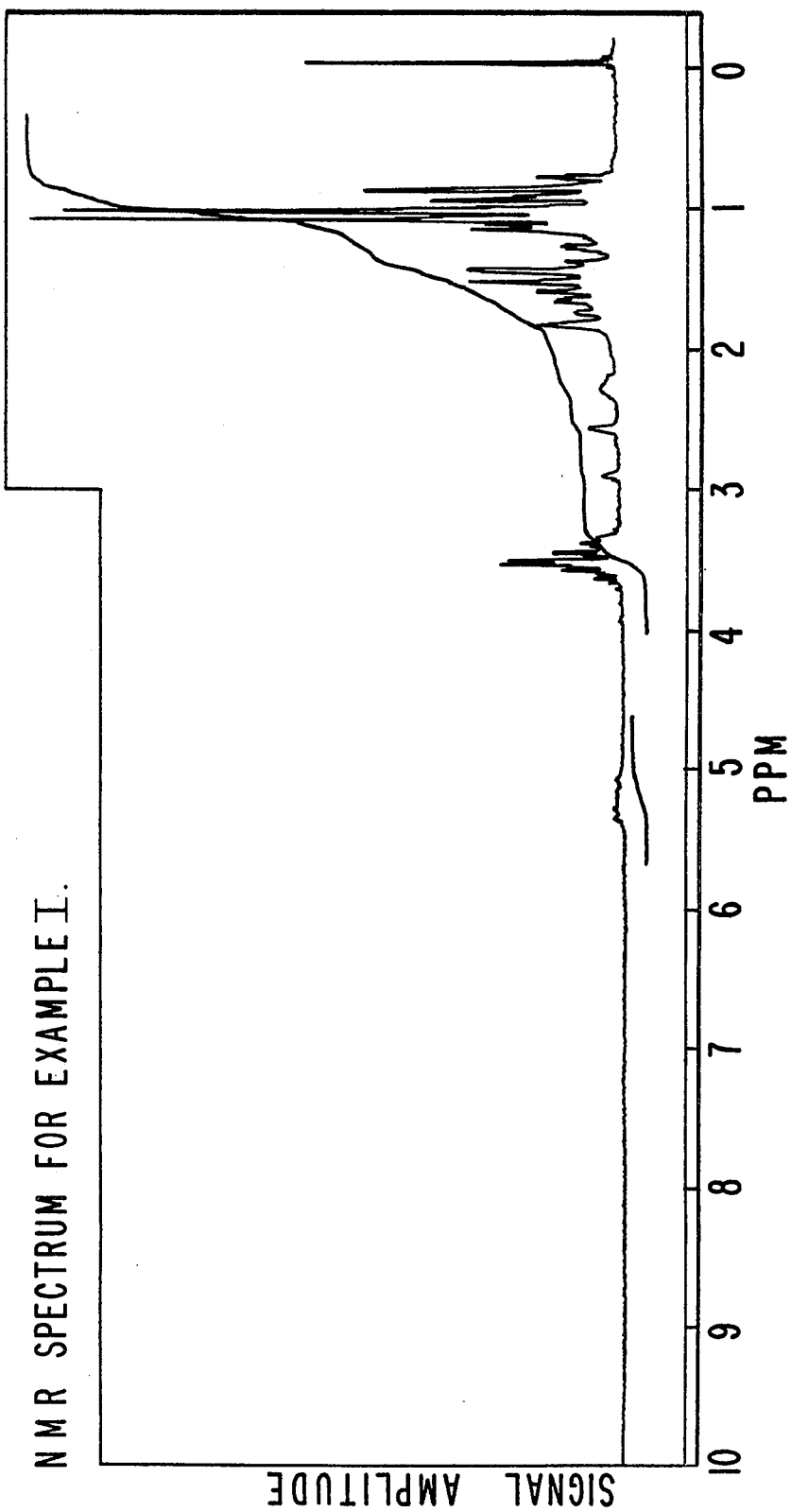

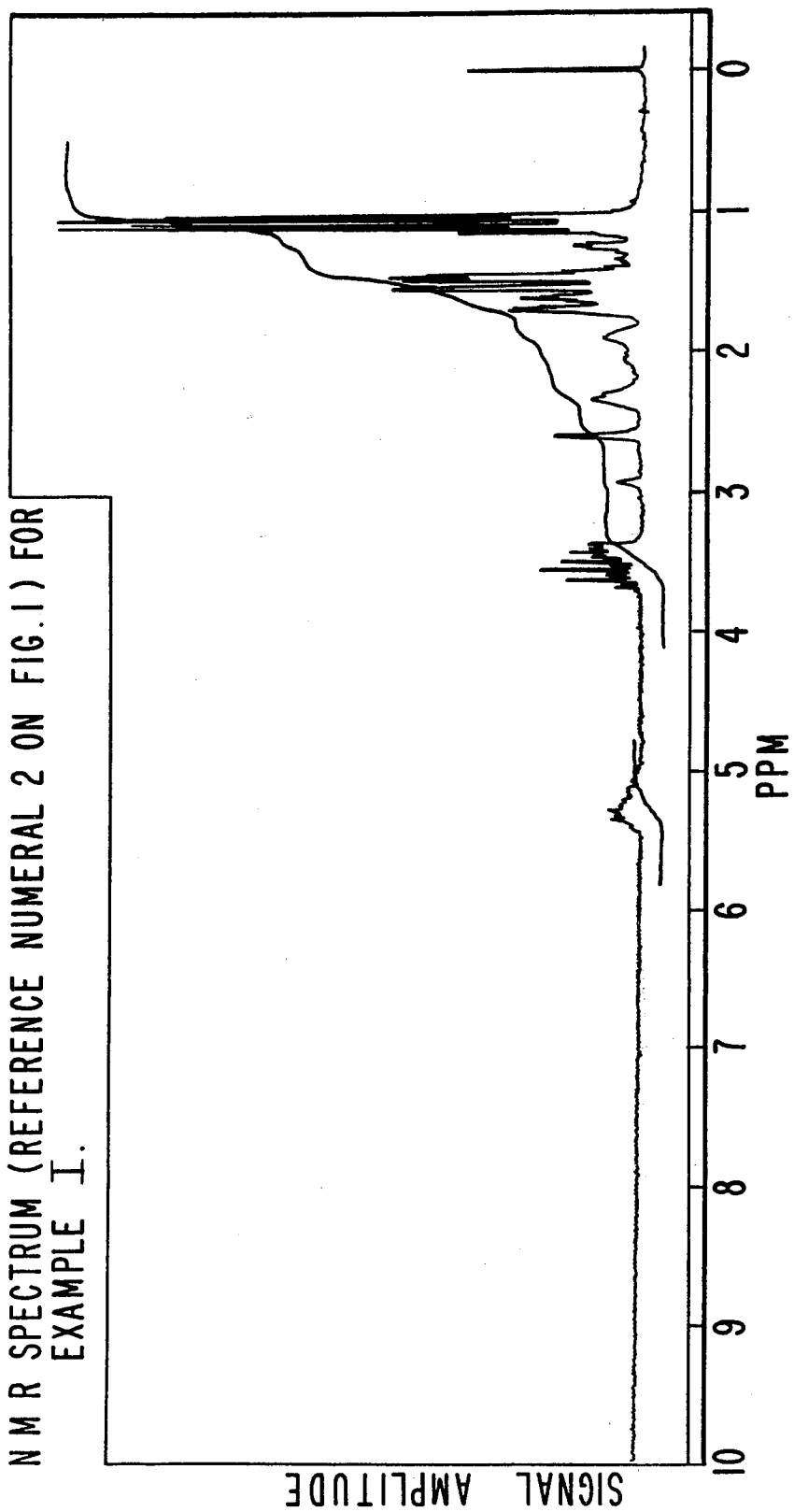

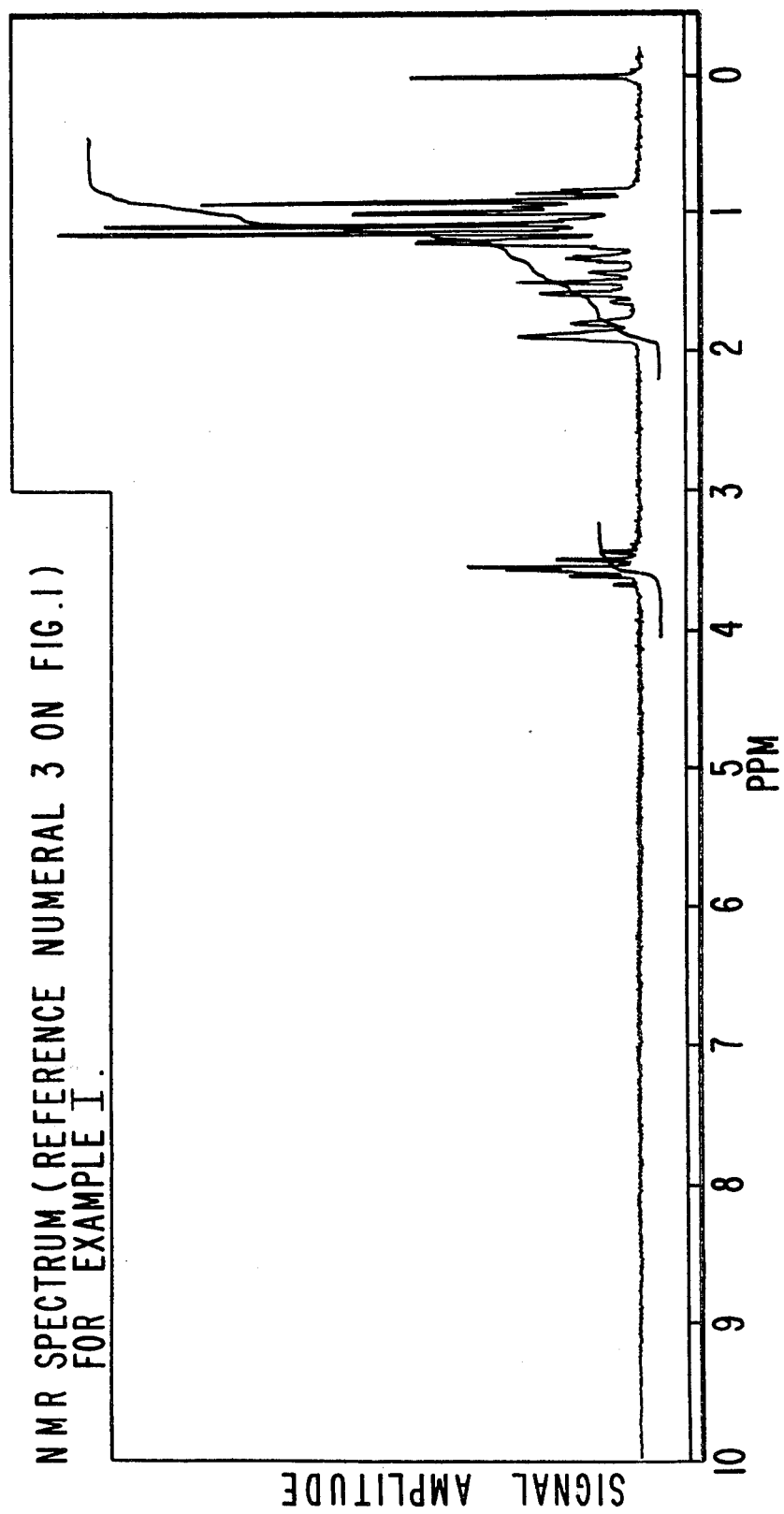

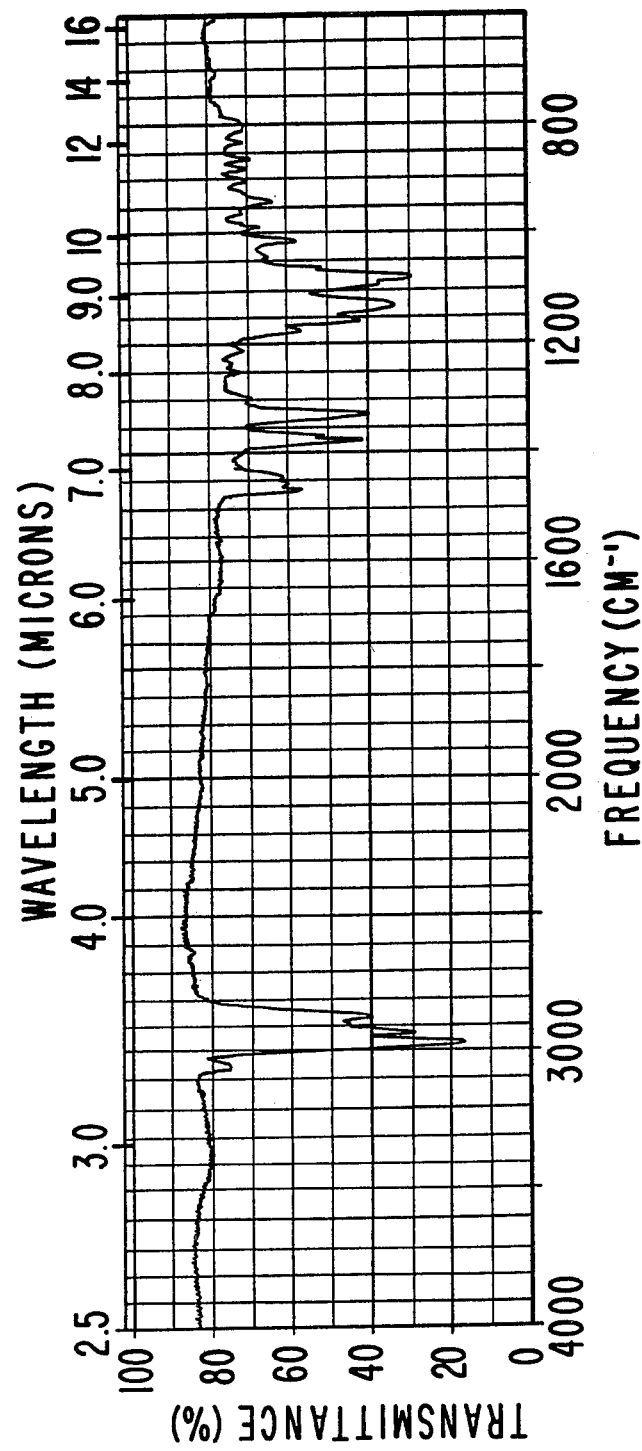

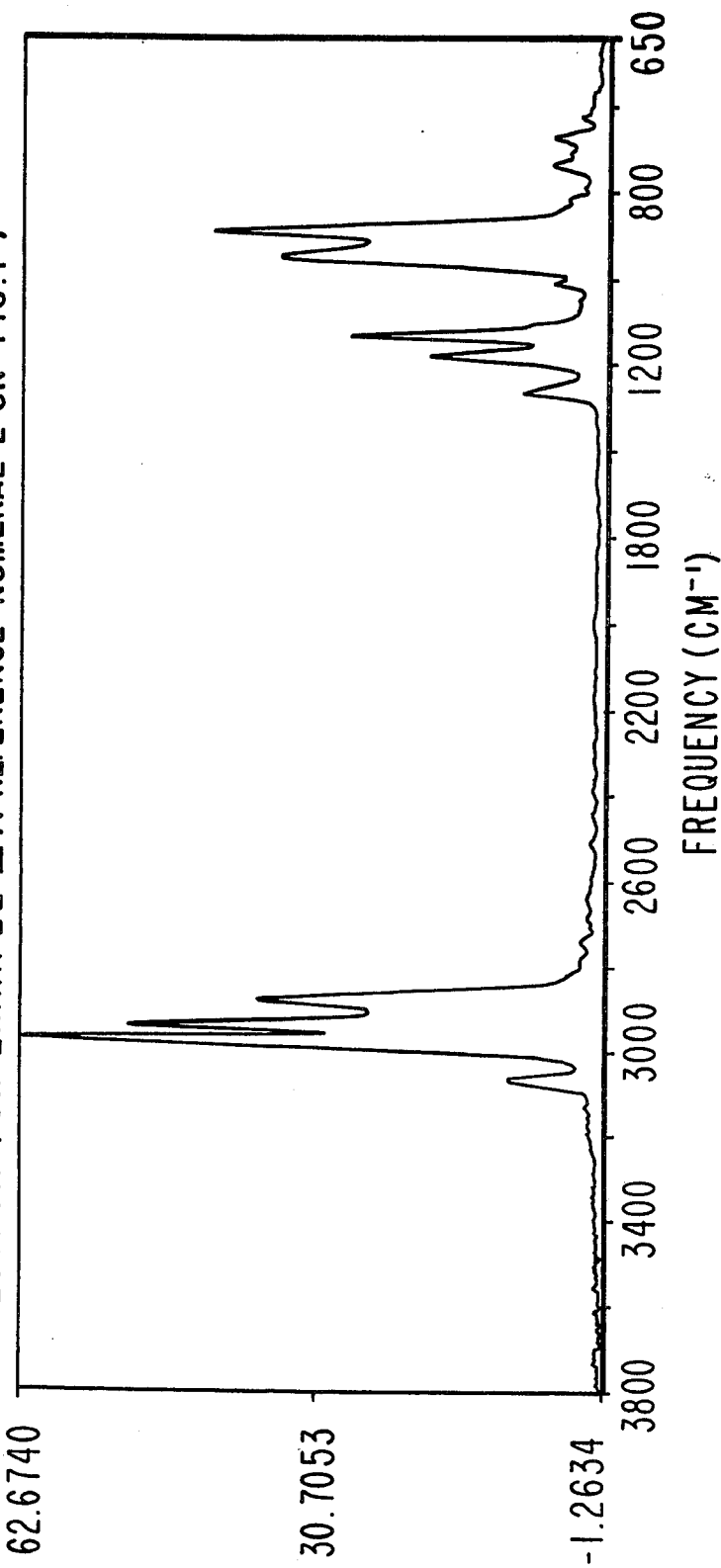

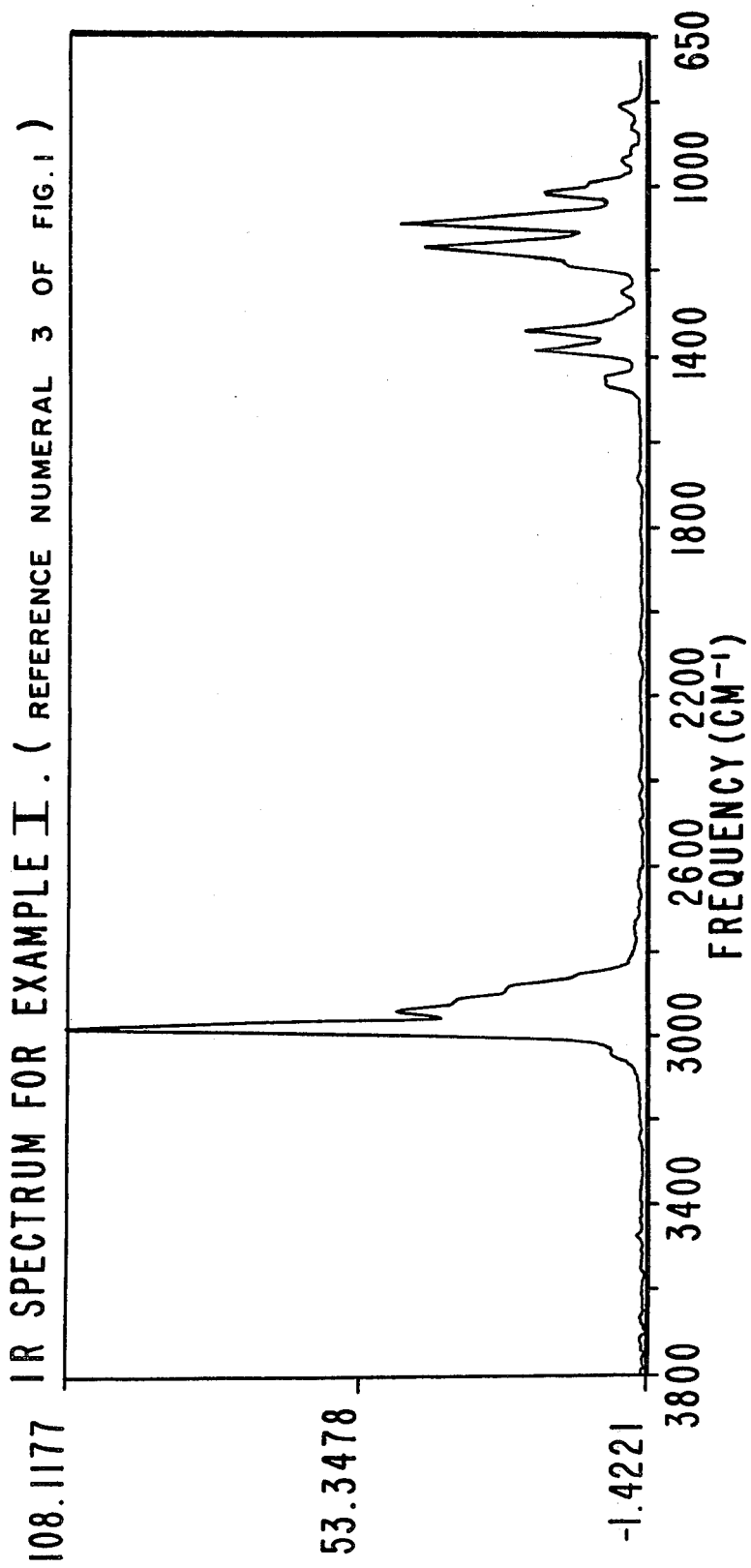

NORBORNYL ALKYL ETHERS

This application is a continuation-in-part of application for U.S. Letters Pat., Ser. No. 200,012 filed on Oct. 23, 1980 and now U.S. Pat. No. 4,311,861.

BACKGROUND OF THE INVENTION

The present invention relates to substituted norbornene ether derivatives of the genus of compounds having the structures:

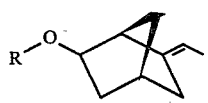

and

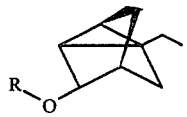

wherein R represents isopropyl.

There has been considerable work performed relating to substances which can be used to impart (modify, augment or enhance) fragrances to (or in) various consumable materials. These substances are used to diminish the use of natural materials, some of which may be in short supply and to provide more uniform properties in the finished product.

Long-lasting, fresh, green bean, rosey, citrus, petit-grain-like, fruity, anisic, green, raw potato-like, twiggy, herbaceous, sweet, sweaty, green pea-like, chocolate-like, carrot-like and creamy aroma nuances with galbanum topnotes and anther-like and anise-like undertones are desirable in several types of perfume compositions, perfumed articles and colognes.

The perfume use of norbornene alcohol and ester derivatives having the structures:

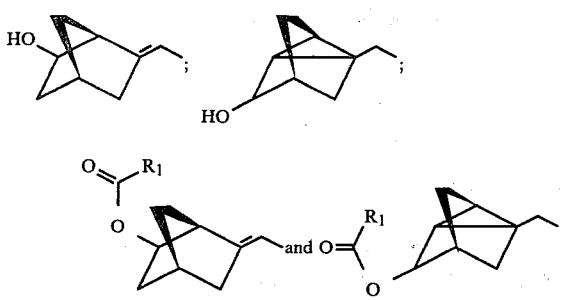

wherein $R_1$ is $C_1$–$C_4$ alkyl is disclosed in U.S. Pat. No. 3,860,635 particularly at Example XV at column 16 thereof. Such compounds and the synthesis thereof are also disclosed by Bobyleva, Zh. Org. Kh. Volume 13, No. 10, pages 2085–92, October 1977. In addition, ethers of norbornene derivatives having the structures:

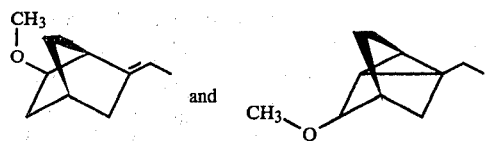

are disclosed as well as the process for preparing same according to the reaction:

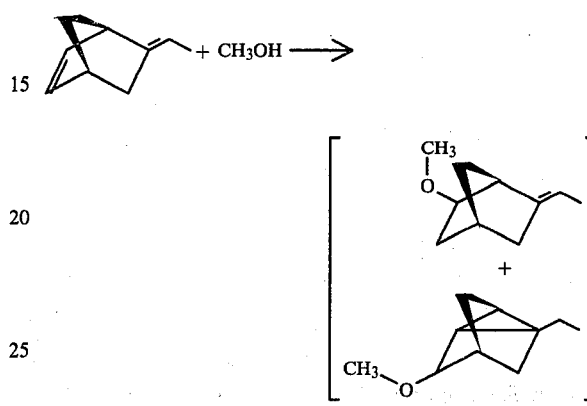

in Shields, Can. J. Chem. Volume 49, 1971, page 1142.

U.S. Pat. No. 3,927,116 indicates the utility of certain vinyl norbornyl ethers having the structure:

wherein $R_2$ represents $C_1$–$C_4$ alkyl as being intermediate for the preparation of detergents at column 9 lines 10–15. No indication in U.S. Pat. No. 3,927,116 of the use of such compounds in perfumery, for augmenting or enhancing the aroma of perfumes, perfumed articles and colognes, is suggested either implicitly or explicitly in U.S. Pat. No. 3,297,116.

Sumitomo Chemical Company, Ltd. Japanese Patent No. J74,020,571 published on May 25, 1974 discloses the reaction:

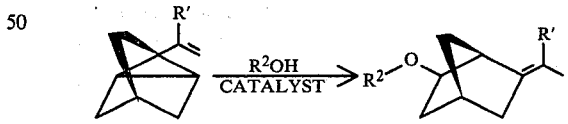

wherein $R^1$ is hydrogen or one to eight carbon alkyl; and $R^2$ is hydrogen, alkyl or acyl. The Sumitomo Patent indicates that the use of the resultant compounds are as intermediates in the production of medicinal agents and agricultural chemicals. Specifically, the Sumitomo Patent discloses 6-ethoxy-2-isopropylidene norbornane having the structure:

No disclosure is set forth in the Sumitomo Patent of the use of the isopropyl ethers of our invention in augmenting or enhancing the aroma of perfumes or augmenting or enhancing organoleptic properties of consumable materials, in general. No disclosure is set forth in the Sumitomo Patent of the use of any of the norbornyl ethers for augmenting or enhancing the aroma or taste of consumable materials.

Thus, the compounds of our invention, having the structures:

and

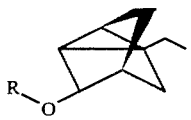

wherein R is isopropyl have unexpected, unobvious and advantageous perfumery properties over any closely similar compounds of the prior art.

BRIEF DESCRIPTION OF THE DRAWINGS

FIG. 1 sets forth the GLC profile for the crude reaction product of Example I containing the compounds having the structures:

and

FIG. 1(A) is the GLC profile of the purified reaction product of Example I containing the compounds having the structures:

and

wherein peak 2 on said FIG. 1(A) is the compound having the structure:

and peak 3 on said FIG. 1(A) consists of the compound having the structure:

FIG. 2 sets forth the NMR spectrum for the reaction product of Example 1(A) containing the compounds having the structures:

and

FIG. 2(A) represents the NMR spectrum for peak 2 of the GLC profile of FIG. 1(A) and consists of the compound having the structure:

FIG. 2(B) is the NMR spectrum for peak 3 of the GLC profile of FIG. 1(A) and consists essentially of the compound having the structure:

FIG. 3 sets forth the infra red spectrum for the reaction product of Example I containing the compounds having the structures:

and

-continued

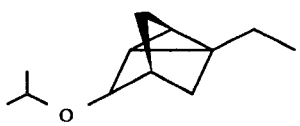

FIG. 3(A) represents the infra red spectrum for peak 2 of the GLC profile of FIG. 1(A) which peak consists essentially of the compound having the structure:

FIG. 3(B) represents the infra red spectrum for peak 3 of the GLC profile of FIG. 1(A) and consists essentially of the compound having the structure:

DETAILED DESCRIPTION OF THE DRAWINGS

FIG. 1(A) is the GLC profile for the reaction product produced according to Example I and contains starting material having the structure:

as well as reaction products:

and

Reference "1" indicates the peak of this GLC profile which consists of the compound having the structure:

Reference "2" indicates the peak of the GLC profile which consists essentially of the compound having the structure:

Reference "3" indicates the peak of the GLC profile which consists essentially of the compound having the structure:

THE INVENTION

The instant invention relates to the use for augmenting or enhancing the aroma of perfumes, perfumed articles and colognes of compunds having the generic structures:

and

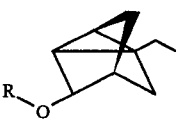

either taken alone or in admixture wherein R represents isopropyl.

These compounds as a group have long lasting, fresh, green bean-like, rosey, citrus, petitgrain-like aromas.

The compounds of our invention may be prepared by reacting ethylidene norbornene having the structure:

with ROH, wherein R represents isopropyl in the presence of a catalyst which is either a mineral acid or a Lewis acid. Examples of mineral acid catalysts are sulfuric acid, phosphoric acid, para-toluene sulfonic acid, methane sulfonic acid and acid ion-exchange resin. Examples of Lewis acid which can be used as catalysts are boron trifluoride etherate, aluminum chloride, zinc chloride, stannic chloride, stannouse chloride, zinc bromide, diethyl aluminum chloride, ethyl aluminum dichloride, ethyl aluminum dibromide and diethyl aluminum bromide. The reaction preferably takes place in the presence of an inert sorvent such as tetrahydrofuran, toluene or benzene. The reaction may take place in the absence of the inert solvent and in the presence of an excess of the alcohol reactant, the excess of the alcohol reactant being used as the "solvent".

The reaction temperature may vary from about 25° C. up to 120° C. with reflux temperature being preferred. The reflux temperature depends upon the pressure in the reactor and the particular solvent being used as well as its concentration. The mole ratio of acid catalyst to ethylidene norbornene may vary from about 1:99 up to about 1:10. The mole ratio of ethylidene norbornene reactant to ROH alcohol reactant may vary from about 1:1 up to about 1:2 with a mole ratio of 1:1.5 of norbornene: alcohol reactant being preferred. Thus, the reaction to produce the compounds of our invention may be shown thusly:

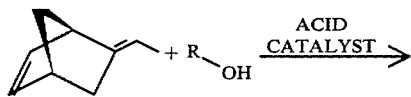

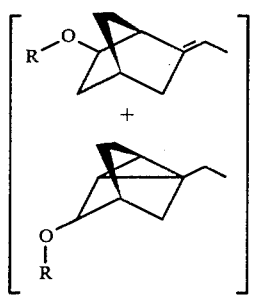

The compounds of our invention are usually prepared in admixture with compounds having the generic structure:

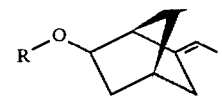

being prepared along with compounds having the structure:

These compounds, however, may be separated by distillation, extraction and preparative GLC techniques in order to yield separately compounds having the structure:

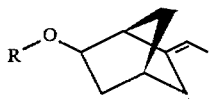

and separate therefrom compounds having the structure:

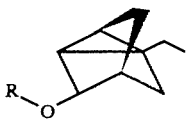

In addition, the compounds having the structures:

and

exist in isomeric forms and are produced in admixture. The mixture of these "endo" and "exo" and "cis" and "trans" isomers may be separated from one another by means of standard separation techniques including preparative GLC techniques whereby the individual isomers may be separated and then utilized individually. Structures of these isomers are as follows:

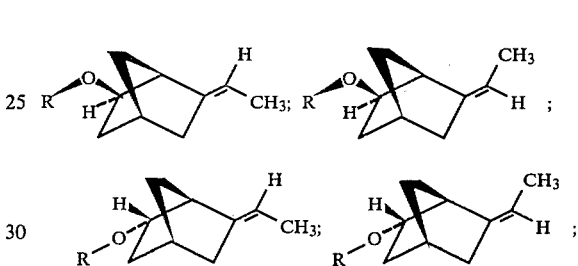

Specific examples of the compounds produced according to the foregoing process and useful for the practice of my invention are set forth in table I below.

TABLE I

| Structure of Compounds | Perfumery Evaluation |
|---|---|
| 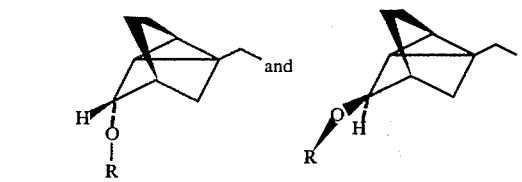 | A fresh, green bean-like rosey, citrus, (petitgrain-like) aroma. |

Produced according to Example I.

The norbornyl ether derivative(s) and one or more auxiliary perfume ingredients, including, for example, hydrocarbons, alcohols, ketones, aldehydes, nitriles, esters, lactones, ethers other than said norbornyl ether derivative(s), hydrocarbons, synthetic essential oils and natural essential oils may be admixed so that the combined odors of the individual components produce a pleasant and desired fragrance, particularly and preferably in citrusy and/or green woody and/or piney fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to their particular olfactory characteristics, however the over-all sensory effect of the perfume composition will be at least the sum total of the effects of each of the ingredients. Thus, one or more of the norbornyl ether derivative(s) of our invention can be used to alter, modify or enhance the aroma characteristic of a perfume composition, for example, by utilizing or moderating the olfactory reaction contributed by another ingredient in the composition.

The amount of norbornyl ether derivative(s) of our invention which will be effective in perfume compositions as well as in perfumed articles and colognes depends upon many factors, including the other ingredients, their amounts and the effects which are desired. It has been found that perfume compositions containing as little as 0.005% of norbornyl ether derivative(s) or even less (e.g., 0.002%) can be used to impart fresh, green bean, rosey, citrus, and petitgrain-like aroma nuances to soaps, cosmetics, detergents (including anionic, nonionic, zwitterionic and cationic solid or liquid detergents), perfumed polymers or other products. The amount employed can range up to 70% of the fragrance components and will depend upon considerations of cost, nature of the end product, the effect desired on the finished product and the particular fragrance sought.

The norbornyl ether derivative(s) of our invention are useful (taken alone or together with other detergents in perfume compositions) in detergents and soaps, space odorants and deodorants, perfumes, colognes, toilet water, bath preparations such as lacquers brilliantines, pomades and shampoos; cosmetic preparations, such as creams, deodorants, hand lotions and sun screens; powders such as talcs, dusting powders, face powders and the like. As little as 0.25% of the norbornyl ether derivative(s) will suffice to impart an intense green, petitgrain-like, rosey and citrusy notes to citrusy, woody, floral and piney perfume formulations. Generally, no more than 5% of the norbonyl ether derivative(s) based on the ultimate end product is required to be used as is or in the perfume composition.

Furthermore, as little as 0.25% of the norbornyl ether derivative(s) will suffice to impart such aroma to perfumed articles per se, whether in the presence of other perfume materials or whether used by itself. Thus, the range of use of the norbornyl ether derivative(s) of our invention in perfumed articles may vary from 0.25% up to 5% by weight based on the total weight of the perfumed article.

In addition, the perfume composition or fragrance composition of our invention can contain a vehicle, or carrier for the nrbornyl ether derivative(s). The vehicle can be a liquid such as a non-toxic alcohol, e.g. ethanol, a non-toxic glycol, e.g. propylene glycol or the like. The carrier can also be an absorbent solid, such as a gum, (e.g. gum arabic), or components for encapsulating the composition by means of coacervation (such as gelatin).

It will thus be apparent that the norbornyl ether derivative(s) of our invention can be utilized to alter, modify or enhance aroma or perfume compositions, colognes or perfumed articles.

Example I, following serves to illustrate the process for specifically producing the norbornyl ether derivative(s) useful in my invention.

The following examples in general, serve to illustrate specific embodiments of my invention. It will be understood that these examples are illustrative and the invention is to be considered restricted thereto only as indicated in the appended claims. All parts and percentages given herewith are by weight unless otherwise specified.

EXAMPLE I

PREPARATION OF A MIXTURE OF 2-ETHYL-5-ISOPROPYLTRICYCLO [2.2.1.0(2,6)]HEPTANE and 2-ETHYLIDENE-6-ISOPROPOXYNORBORNANE Reaction:

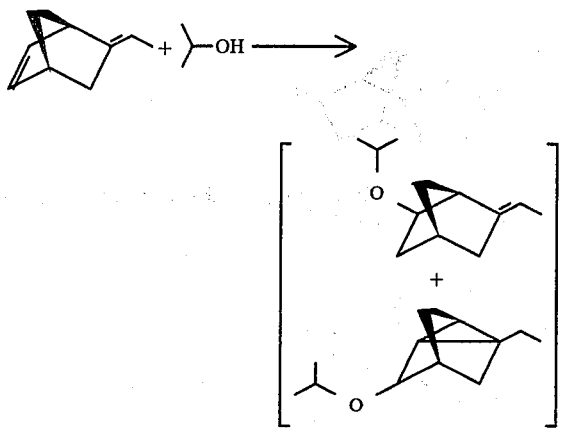

Vinylidene norbornene (480 grams) is added over a 90 minute period to a stirred solution of isopropanol (300 grams) and boron trifluoride etherate (12 grams) at reflux (temperature varies from 75° C. to 97° C.). The reaction mass is quenched with 1 liter of water. The organic layer is subsequently washed with 500 ml of 10% NaOH. Distillation through a 1½"×12" Goodloe ® packed column affords 651 grams of product (b.p. 75° C. at 5 mmHg pressure).

FIG. 1 sets forth the GLC profile for the crude reaction product of Example I containing the compounds having the structures:

and

-continued

FIG. 1(A) is the GLC profile of the purified reaction product of Example I containing the compounds having the structures:

and

wherein peak 2 on said FIG. 1(A) is the compound having the structure;

and peak 3 on said FIG. 1(A) consists of the compound having the structure:

FIG. 2 sets forth the NMR spectrum of the product mixture consisting of 2-ethyl-5-isopropyltricyclo[2.2.1.0$^{(2,6)}$]heptane and 2-ethylidene-6-isopropoxynorbornane having respectively, the structures:

and

FIG. 2(A) sets forth the NMR spectrum for peak 2 of the GLC profile of FIG. 1(A) consisting of the compound having the structure:

FIG. 2(B) sets forth the NMR spectrum for peak 3 of the GLC profile of FIG. 1(A) consisting of the compound having the structure:

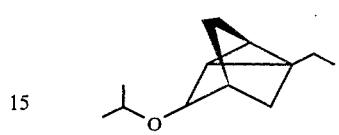

FIG. 3 sets forth the infra red spectrum of the product mixture consisting of 2-ethyl-5-isopropyltricyclo [2.2.1.1$^{(2,6)}$]heptane and 2-ethylidene-6-isopropoxynorbornane.

FIG. 3(A) sets forth the infra red spectrum for peak 2 of the GLC profile of FIG. 1(A) consisting of the compound having the structure:

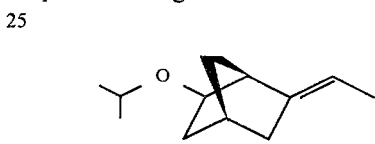

FIG. 3(B) sets forth the infra red spectrum for peak 3 of the GLC profile of FIG. 1(A) consisting of the compound having the structure:

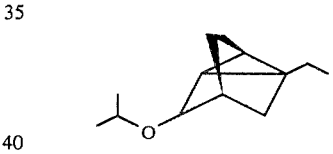

EXAMPLE II

The following formulation is prepared:

| Ingredients | Parts by Weight |
|---|---|
| Turpentine gum oil | 100 |
| Limonene | 70 |
| Gum camphor | 10 |
| Isobornyl acetate | 50 |
| Borneol | 30 |
| 2-(2-Butenoyl)-3,3-dimethylnorbornane (Produced according to Example XII of U.S. Pat. No. 4,148,826) | 40 |
| Mixture of 2-(3-butenoyl)-3,3-dimethylnorbornane and 2-(2-butenoyl)-3,3-dimethylnorbornane (Produced according to the process of Example III of U.S. Pat. No. 4,148,826) | 100 |
| Alpha-allyl-3,3-dimethyl-2-norbornanemethanol (Produced according to the process of Example II of U.S. Pat. No. 4,148,826) | 70 |
| The products produced according to Example 1, containing compounds having the structures: | |

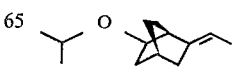

and

| Ingredients | Parts by Weight |
|---|---|
|  | 60 |

The above composition has an interesting pine needle oil aroma with a fresh, green bean-like, rosey, citrusy, petitgrain-like aroma.

EXAMPLE III

PREPARATION OF A COSMETIC POWDER PREPARATION

A cosmetic powder is prepared by mixing in a ball mill, 100 g of talcum powder with 0.25 g of one of the substances set forth in Table II below. The resulting cosmetic powder has a pleasant aroma as set forth in Table II below.

TABLE II

| Structure of Compounds | Perfumery Evaluation |
|---|---|
| 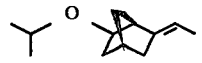 and  Produced according to Example I | A fresh, green bean-like rosey, citrus, (petitgrain-like) aroma. |

| Example | Aroma nuance |
|---|---|
| Perfumed Composition Prepared According to Example II | A pine needle oil aroma with fresh, green bean-like, rosey, citrusy and petitgrain-like nuances. |

EXAMPLE IV

Concentrated liquid detergents (Lysine salt of n-dodecylbenzene sulfonic acid as more specifically described in U.S. Pat. No. 3,948,818, issued on April 6, 1976 the disclosure of which is incorporated herein by reference) with fragrance profiles as defined in Table II of Example III, supra, are prepared containing 0.10%, 1.15%, 0.20%, 0.25%, 0.30% and 0.35% of the substances as set forth in Table II, supra. They are prepared by adding and homogeneously mixing the appropriate quantity of substance as set forth in Table II, supra, in the liquid detergent. The detergents all possess excellent intense aromas as defined according to the profiles of Table II, supra, the intensity increasing with greater concentrations of said substance as set forth in Table II, supra.

EXAMPLE V

PREPARATION OF A COLOGNE AND HANDKERCHIEF PERFUME

Substances set forth in Table II, supra, are each individually incorporated into colognes at concentrations of 2.0%, 2.5%, 3.0%, 3.5%, 4.0%, 4.5% and 5.0% in (75%, 80%, 85% and 90%, aqueous food grade ethanol solutions); and into handkerchief perfumes at concentrations of 15%, 20%, 25%, and 30% (in 80%, 85%, 90% and 95% aqueous food grade ethanol solutions). Distinctive and definitive long-lasting aromas as defined according to Table II, supra, are all imparted to the cologne and to the handkerchief perfumes at all levels as indicated above.

EXAMPLE VI

PREPARATION OF SOAP COMPOSITION

One hundred grams of soap chips (IVORY ®, produced by the Procter & Gamble Company of Cincinnati, Ohio) are admixed with one gram of each of the substances separately, as set forth in Table II, supra, until homogenous compositions are obtained. In each of the cases, the homogeneous compositions are heated under eight atmospheres pressure at 180° C. for a period of three hours and the resulting liquids are placed into soap molds. The resulting soap cakes, on cooling, manifest excellent, long-lasting aromas as set forth in Table II, supra.

EXAMPLE VII

PREPARATION OF SOLID DETERGENT COMPOSITIONS

Detergents are prepared from the following ingredients according to Example I of Canadian Pat. No. 1,007,948 (the disclosure of which is incorporated herein by reference):

| Ingredient | Percent by Weight |
|---|---|
| Neodol ® 45-11 (a $C_{14}$-$C_{15}$ Alcohol ethoxylated with 11 moles of ethylene oxide) | 12 |
| Sodium carbonate | 55 |
| Sodium citrate | 20 |
| Sodium sulfate, water brighteners | q.s. |

This detergent is a "phosphate-free" detergent. A total of 100 grams of said detergent is admixed with 0.10, 0.15, 0.20 and 0.25 grams of each of the substances set forth in Table II, supra. Each of the detergent samples have excellent aromas as indicated in Table II, supra.

EXAMPLE VIII

Utilizing the procedure of Example I, at Column 15 of U.S. Pat. No. 3,632,396 (the disclosure of which is incorporated by reference herein), a non-woven cloth substrate useful as a dryer-added fabric softening article of manufacture is prepared wherein the substrate, the substrate coating and the outer coating and the perfuming material are as follows:
1. A water "dissolvable" paper (Dissolvo Paper")
2. Adogen 448 (m.p. about 140° F.) as the substrate coating; and
3. An outer coating having the following formulation (m.p. about 150° F.):
   57 percent $C_{20}$-$C_{22}$ HAPS
   22 percent isopropyl alcohol
   20 percent antistatic agent
   1 percent of one of the substances as set forth in Table II, supra.

Fabric softening articles containing substances as set forth in Table II, supra, essentially consist of a substrate consisting essentially of the water dissolvable paper having a weight of 3 grams per 100 square inches; a substrate coating having a weight of about 1.85 grams per 100 square inches of substrate; and an outer coating coated on the substrate coating having a weight of about 1.4 grams per 100 square inches of substrate are prepared. The total aromatized substrate and outer coating has a weight ratio of about 1:1.

The aromas set forth in Table II, supra, are imparted in a pleasant manner, to the head space in a dryer on operation thereof, using the said dryer-added fabric softening non-woven fabric.

EXAMPLE IX

Four drops of one of the sustances set forth in Table II, supra, are added to 2 grams of Aromox ®DMC-W to produce a clear premix. The clear premix is added to 200 grams of CLOROX ® with stirring resulting in a clear stable, single phase solution. Sufficient 1 M aqueous NaOH is added to bring the pH of the mixture up to 12.8. The solution remains substantially stable at 120° F. for a period seven days. When the 5% aqueous sodium hypochlorite solution is used as a laundry bleach, the resulting laundry, on dry-out in an atmosphere of 65% relative humidity yields substantially no characteristic "hypochlorite" odor, but does have a faint pleasant aroma as set forth in Table II, supra. Furthermore, no such characteristic "hypochlorite" aroma is retained on the hands of the individual handling such laundry in both the wet and the dry states.

EXAMPLE X

SCOURING CLEANSER COMPOSITION

A scouring cleanser composition is prepared in accordance with Example I, at Columns 11 and 12 of U.S. Pat. No. 4,193,888, issued on Mar. 18, 1980 (the disclosure of which is incorporated by reference herein). To this composition, a substance as set forth in Table II, supra, is added at the level of 0.25% as set forth in the Table in said Example I of U.S. Pat. No. 4,193,888 yielding an aroma on using said cleaner in ordinary circumstances which is quite pleasant and described in Table II, supra.

EXAMPLE XI

A fabric softening article prepared substantially as set forth in Example VIII of Canadian Pat. No. 1,069,260 (the disclosure of which is incorporated by reference herein) is prepared, containing 0.21 percent by weight of a perfuming substance as set forth in Table II, supra, and yielding on use in a dryer, a faint aroma as set forth in Table II, supra.

EXAMPLE XII

COMPARISON FROM A PERFUMERY STANDPOINT OF THE COMPOUNDS OF THIS INVENTION WITH THE COMPOUNDS OF THE PRIOR ART

The following compositions are prepared:

Composition 1A—A mixture of compounds is produced according to Example I, supra, defined according to the structure:

(product-by-process)

wherein in the mixture in each of the molecules, one of the dashed lines represents a carbon-carbon bond and the other of the dashed lines represents no bond.

Composition 1B—The compound prepared according to Example I, supra, having the structure:

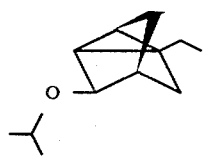

Composition 1C—The compound prepared according to Example I, supra, having the structure:

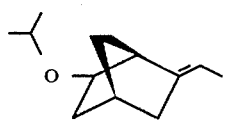

Composition 2A—A mixture of compounds having the structure:

(product-by-process)

wherein in the mixture in each of the molecules, one of the dashed lines represents a carbon-carbon bond and the other of the dashed lines represents no bond prepared according to Example A, infra.

Composition 2B—The compound having the structure:

produced according to Example A, infra.

EXAMPLE A

Reaction:

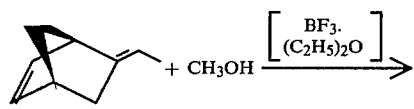

wherein in the mixture produced in each of the compounds, one of the dashed lines is a carbon-carbon bond and the other of the dashed lines represents no bond.

Into an one-liter reaction flask equipped with stirrer, thermometer, reflux condenser and heating mantle is placed 20 grams of boron trifluoride diethyl ether complex and 192 grams of anhydrous methanol. The resulting mixture is heated to reflux (approximately 61° C.). Over a period of one hour, dropwise, is added to the reaction mass, 480 grams of ethylidene norbornene (4 moles). The reaction mass is stirred for a period of four hours at reflux. The reaction mass is then quenched with 400 ml water. The resulting two phases are separated and the oil phase is washed with 200 ml 10% sodium hydroxide solution. The reaction product is then distilled on a 12"×1.5" Goodloe column yielding the following fractions:

| Fraction No. | Vapor Temp. (0° C.) | Liquid Temp. (0° C.) | Vacuum mm Hg Pressure | Reflux Ratio | Fractions (Grams) |
|---|---|---|---|---|---|
| 1 | 35/54 | 58/62 | 11 | 4:1 | 58.4 |
| 2 | 52 | 65 | 11 | 4:1 | 31.8 |
| 3 | 54 | 64 | 10 | 4:1 | 31.7 |
| 4 | 57 | 64 | 10 | 100% | 45.6 |
| 5 | 57 | 63 | 10 | 100% | 44.7 |
| 6 | 57 | 64 | 10 | 100% | 48.5 |
| 7 | 58 | 65 | 10 | 100% | 46.7 |
| 8 | 58 | 66 | 10 | 100% | 54.7 |
| 9 | 58 | 68 | 10 | 100% | 52.6 |
| 10 | 60 | 93 | 10 | 100% | 53.1 |
| 11 | 60 | 101 | 10 | 100% | 36.3 |
| 12 | 61 | 112 | 10 | 100% | 4.7 |

Fractions 6-10 are bulked for evaluation.

Composition 2C—The compound having the structure:

produced according to Example A, infra.

Composition 3A—A mixture of compounds defined according to the structure:

(product-by-process)

prepared according to Example B, infra, wherein one of the dashed lines represents a carbon-carbon bond and the other of the dashed lines in each of the compounds of the mixture represents no bond.

EXAMPLE B

Reaction:

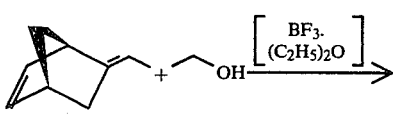

wherein in the resulting mixture in each of the molecules, one of the dashed lines represents a carbon-carbon bond and the other of the dashed lines represents no bond.

Into an one liter reaction flask equipped with reflux condenser, stirrer, thermometer and heating mantle is placed 276 grams of anhydrous ethanol (6 moles) and 20 ml boron trifluoride diethyl ether complex. The resulting mixture is heated to reflux and over a forthy minute period while refluxing, ethylidene norbornene (480 grams; 4 moles) is added to the reaction mass. The reaction mass is then refluxed for a period of 2.5 hours. At the end of the refluxing period, 300 ml water is added to the reaction mass. The resulting mixture separates into two phases, an aqueous phase and an organic phase. The organic phase is separated and washed with 200 ml 10% Na OH solution. The resulting product is then dried and distilled on a 12"×1.5" Goodloe column yielding the following fractions.

| Fraction No. | Vapor Temp. (0° C.) | Liquid Temp. (0° C.) | Vacuum mm Hg Pressure | Reflux Ratio | Fractions (Grams) |
|---|---|---|---|---|---|
| 1 | 28/62 | 119/71 | 10 | 4:1 | 49.0 |
| 2 | 61 | 72 | 10 | 4:1 | 34.3 |
| 3 | 61 | 72 | 10 | 4:1 | 45.0 |
| 4 | 66 | 73 | 10 | 100% | 48.0 |
| 5 | 67 | 73 | 10 | 100% | 52.0 |
| 6 | 67 | 73 | 10 | 100% | 57.2 |
| 7 | 67 | 73 | 10 | 100% | 55.4 |
| 8 | 68 | 77 | 10 | 100% | 41.0 |
| 9 | 69 | 78 | 10 | 100% | 56.5 |
| 10 | 70 | 80 | 10 | 100% | 47.4 |
| 11 | 70 | 130 | 10 | 100% | 56.5 |
| 12 | 68 | 137 | 10 | 100% | 22.0 |

Fractions 7-10 are bulked.

Composition 3B—The compound having the structure:

prepared according to Example B, infra.

Composition 3C—The compound having the structure:

prepared according to Example B, infra.

Composition 4A—A mixture of compounds defined according to the structure:

(product-by-process)

prepared according to the process of Example C, infra, wherein in each of the compounds of the mixture one of the dashed lines represents a carbon-carbon bond and the other of the dashed lines represents no bond.

Composition 4B—The compound having the structure:

prepared according to the process of Example C, infra.

Composition 4C—The compound having the structure:

prepared according to the process of Example C, infra.

EXAMPLE C

Reaction:

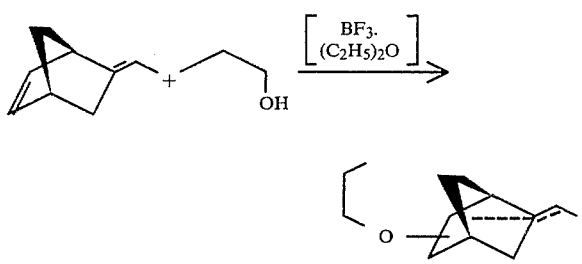

wherein in the mixture in each of the molecules, one of the dashed lines represents a carbon-carbon bond and the other of the dashed lines represents no bond.

Into an one liter reaction flask equipped with stirrer, thermometer, reflux condenser and heating mantle is placed 348 grams (6 moles) of n-propanol and 20 ml boron trifluoride diethyl ether complex. The resulting mixture is heated to reflux (95° C.). Over a 45 minute period, is added 480 grams (4 moles) of ethylidene norbornene dropwise. The reaction mass is then quenched with water. The resulting organic phase is separated from the aqueous phase and the organic phase is washed with 200 ml 10% sodium hydroxide. The resulting product is dried and distilled on a 12"×1.5— Goodloe column to yield the following fractions:

| Fraction No. | Vapor Temp. (0° C.) | Liquid Temp. (0° C.) | Vacuum mm Hg Pressure | Reflux Ratio | Fractions (Grams) |
|---|---|---|---|---|---|
| 1 | 26/78 | 54/87 | 10 | 4:1 | 58.7 |
| 2 | 78 | 88 | 10 | 4:1 | 45.0 |
| 3 | 78 | 88 | 10 | 4:1 | 46.8 |
| 4 | 79 | 89 | 10 | 4:1 | 56.5 |
| 5 | 78 | 92 | 10 | 4:1 | 38.6 |
| 6 | 81 | 95 | 10 | 100% | 113.3 |
| 7 | 81 | 97 | 10 | 100% | 80.7 |
| 8 | 81 | 120 | 10 | 100% | 79.9 |
| 9 | 70 | 175 | 10 | 100% | 43.8 |

Fractions 4–7 are bulked.

An investigation is carried out consisting of adding in various concentrations each of the twelve reaction products set forth, supra, to water or ethanol or a mixture thereof thereby forming test solutions. Each of the test solutions is placed on a blotter, and smelled at various points in time from 10 minutes after removing the blotter from solution, up to 2 weeks after removing the blotter from the solution. The results of this investigation are as follows:

| Substance Compared | Aroma |
|---|---|
| Composition 1A | A fresh, citrus, herbaceous, green bean aroma profile. |
| Composition 1B | A fresh, green, green bean, herbaceous, citrus (lemonly) aroma profile. |
| Composition 1C | A metallic, potato-like, galbanum-like, eucalyptol-like, costus oil-like aroma. |
| Composition 2A | A very powerful solventy, harsh, metallic, ketonic aroma profile. |
| Composition 2B | A solventy (low molecular weight ketone-like) low keyed dusty, slightly woody, heptaldehyde-like aroma profile. |
| Composition 2C | A harsh, green, ketonic, slight linalyl-like aroma profile. |
| Composition 3A | A green, gasy aroma with ketonic (e.g., acetone-like) notes; lacking green bean and lemon-like notes. |
| Composition 3B | A very volatile green, aniseed-like aroma. |
| Composition 3C | A pyridine-like, fruity, nutty, dirty hair-like aroma with camphoraceous undertones. |
| Composition 4A | A harsh anise-like, sweet, metallic aroma lacking fresh, clean, herbaceous notes but having a strong fruity nuance. |
| Composition 4B | An aniseed-like, woody aroma with a slight fruity character. |
| Composition 4C | A light, fresh, slightly herbaceous aroma longer lasting than substance 3B. |

In view of the foregoing comparisons one having ordinary skill in the art may conclude that the substances defined according to the formulae:

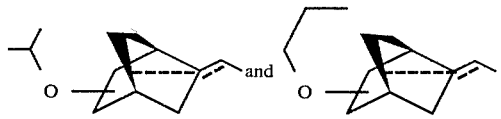

either individually or in admixture with one another (wherein in each of the molecules, one of the dashed lines is a carbon-carbon bond and the other of the dashed lines represents no bond) are unexpectedly, unobviously and advantageously useful for augmenting or enhancing the aroma of perfume compositions given the knowledge of the compounds defined according to the structures:

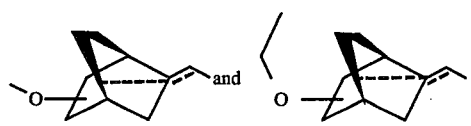

either taken alone or taken in combination wherein in each of the indicated molecules, one of the dashed lines is a carbon-carbon bond and the other of the dashed lines represents no bond.

What is claimed:

1. A product comprising a composition of matter produced according to a process of intimately admixing ethylidene norbornene compound defined according to the structure:

with an alcohol defined according to the structures:

R—OH in the presence of a mineral acid catalyst or a Lewis acid catalyst and in the presence of an inert solvent or in the present of an excess of the alcohol reactant, the reaction temperature varying from about 25° C. up to 120° C., the mole ratio of catalyst to ethylidene norbornene having the structure:

varying from about 1:99 up to about 1:10; the mole ratio of ethylidene norbornene reaction to ROH alcohol reactant varying from about 1:1 up to about 1:2, the moiety R being isopropyl.

2. A composition of matter which is a mixture of two compounds having the structures:

and

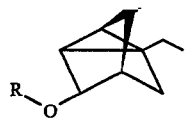

wherein R represents isopropyl.

3. A compound having the structures: